United States Patent [19]

Kawabata et al.

[11] Patent Number: 5,691,205
[45] Date of Patent: Nov. 25, 1997

[54] FLUOROMETRIC ANALYSIS OF CHLORIDE ION AND CHEMICAL SENSOR THEREFOR

[75] Inventors: Yuji Kawabata, Isehara; Yoshiyuki Toge, Sagamihara, both of Japan

[73] Assignee: Canon Kabushiki Kaisha, Tokyo, Japan

[21] Appl. No.: 493,346

[22] Filed: Jun. 21, 1995

[30] Foreign Application Priority Data

Jun. 23, 1994 [JP] Japan .................................. 6-141370
Sep. 7, 1994 [JP] Japan .................................. 6-213768
Apr. 7, 1995 [JP] Japan .................................. 7-082422
May 1, 1995 [JP] Japan .................................. 7-107455

[51] Int. Cl.$^6$ .......................... G01N 33/00; G01N 21/76
[52] U.S. Cl. .......................... 436/125; 436/124; 436/164; 436/165; 436/169; 436/172; 436/800; 422/56; 422/82.05; 422/82.06; 422/82.07; 422/82.08; 422/82.11; 250/458.1; 250/459.1
[58] Field of Search .................... 436/124, 125, 436/164, 165, 169, 170, 172, 800; 422/55, 56, 82.05–82.08, 82.11; 435/808, 288.7; 250/458.1, 459.1; 356/311, 317

[56] References Cited

U.S. PATENT DOCUMENTS 4,580,059  4/1986  Wolfbeis et al. ..................... 250/459.1

FOREIGN PATENT DOCUMENTS 9013809  11/1990  WIPO .

OTHER PUBLICATIONS

Biwersi et al. *Analytical Biochemistry*, vol. 219, May 1994, pp. 139–143.
Kao et al. (abstract CA # 117:2 2691) From *Proc. SPIE–Int. Soc. Opt. Eng.* vol. 1648, 1992, pp. 194–201.
Analytical Chemistry, Edmund Urbano et al., Mar. 1984, vol. 56, No. 3, pp. 427–429, "Optical Sensor for Continuous Detrmination of Halides".

Analytical Chemistry, vol. 62, No. 18, Sep. 15, 1990, pp. 2054–2055, "Ion–Selective Optrode Using Hexadecyl–Acridine Orange Attached on Poly(vinyl chloride) Membrane".

Journal of the Chemical Society of London, vol. VII, pp. 174–184, "Stokes on a Certain Reaction of Quinine", 1869.

Analytical Chemistry, vol. 57, No. 13, Nov. 1985, pp. 2556–2561, O. S. Wolfbeis et al., "Fiber Optical Fluorosensor for Determination of Halothane and/or Oxygen".

Analytical Methods and Instrumentation, vol. 1, No. 1, 60–72 (1993), H. M. Widmer, "Ion–Selective Electrodes and Ion Optodes".

*Primary Examiner*—Maureen M. Wallenhorst
*Attorney, Agent, or Firm*—Fitzpatrick Cella Harper & Scinto

[57] ABSTRACT

Provided is a fluorometric analytical method for detecting chloride ion in a sample by quenching of fluorescence of a fluorescent dye, the fluorescent dye being one of 3,6-bis(dimethylamino)acridine and a derivative thereof of the formulae

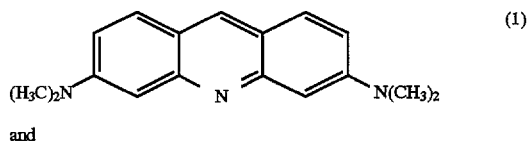

and

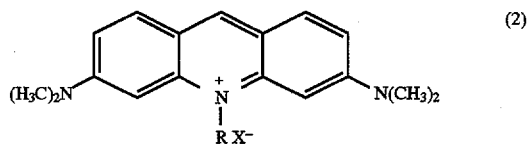

wherein R is alkyl having 1 to 30 carbon atoms, and $X^-$ is a halogen ion.

23 Claims, 5 Drawing Sheets

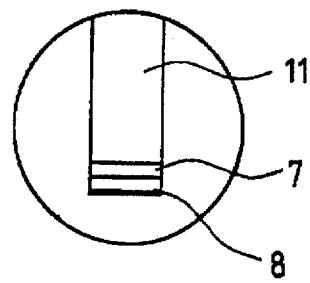
FIG. 8A
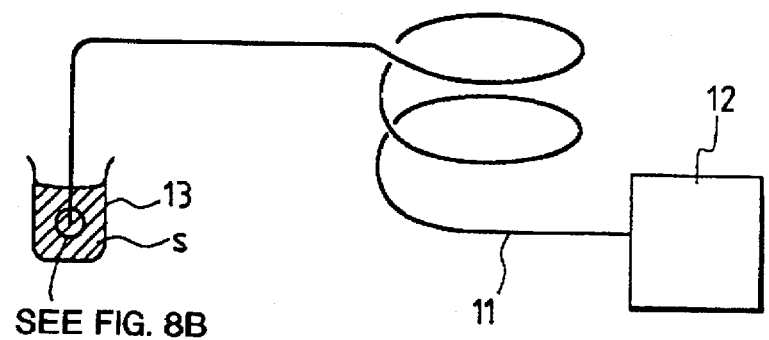
FIG. 8B
FIG. 9
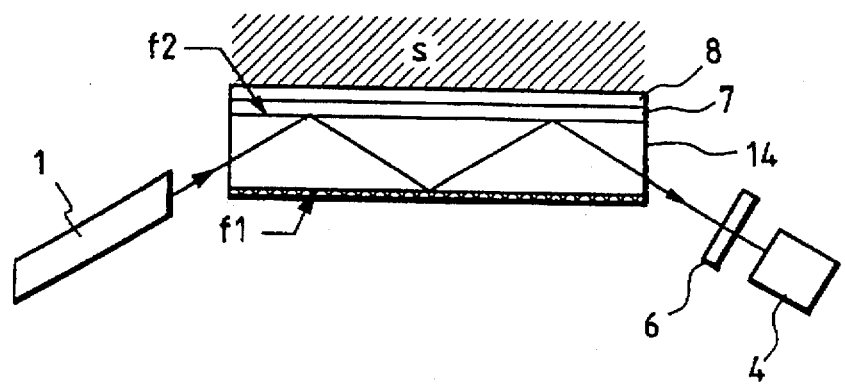

FLUOROMETRIC ANALYSIS OF CHLORIDE ION AND CHEMICAL SENSOR THEREFOR

BACKGROUND OF THE INVENTION

1. Field of the Invention

The present invention relates to a method of selective fluorometric analysis of chloride ion. More specifically, the present invention relates to a method for measuring chloride ion concentration continuously in a sample having a complicated composition.

The present invention also relates to a chemical sensor for chloride ion, in particular, to a chemical sensor based on the fluorometric method.

2. Related Background Art

Chloride ion distributes widely in living bodies, environmental water including river water and sea water, and so forth. A chloride ion is deeply concerned with ecosystems in pH balance, etc. A chloride ion plays an important role as the counter ion to metal ions such as sodium ion and various organic cations. Therefore, a chloride ion concentration is an important index in a variety of technical fields including clinical analysis and environmental protection. Analysis of chloride ion is also important in process control and quality control in industries using hydrochloric acid and metal chloride such as sodium chloride.

In medical treatment or industrial process control, a chloride ion concentration is necessary to be controlled by monitoring the chloride ion continuously and feeding back the analytical results.

Biological samples such as serum, environmental water samples such as river water, industrial samples such as reaction solutions of plants and industrial waste water to be analyzed have a complicated chemical composition, and coexisting ions and organic substances frequently interfere with the analysis seriously. Therefore, an analytical method of chloride ion is demanded which is little affected by coexisting substances. In particular, in the chemical production of the high-purity reagent for semiconductor industries, measurement of chloride ion with high precision is indispensable even in the presence of other halogen ions.

Usually, chloride ion in a water sample is analyzed by gravimetry, titrimetry, or colorimetry. These analytical methods, which have high sensitivity and high precision, require complicated operation in steps of sample preparation, pretreatment, and analysis. For example, colorimetry by a mercury thiocyanate method involves steps of pretreatment of a sample solution, addition thereto of a mercury thiocyanate solution and an iron alum solution, and measurement of absorbance after a prescribed time. In any analytical method, pretreatment of the sample solution is important. In particular, the chloride ion has to be separated from bromide ion, iodide ion and cyanate ion. Accordingly these methods are not readily available to continuous measurement of concentrations of chloride ion in many application fields which require in situ or on line analysis.

On the other hand, electrochemical analysis of chloride ion employing an ion-selective electrode is simple and suitable for continuous measurement, and is conventionally employed for measurement of chloride ion. However, the ion-selective electrode is not so strong mechanically, and is fragile, so that it is less handleable in practical use. Moreover, the measurement is seriously affected by pH of a water sample, and coexisting ions, especially bromide ion and iodide ion. Thus the ion-selective electrode involves many problems in practical use.

Another method for continuous determination of chloride ion concentration with higher selectivity is a method utilizing fluorescence quenching of a fluorescent dye by chloride ion. The phenomenon of fluorescence quenching by chloride ion was firstly reported in the old year of 1869 (Stokes, G. G., et al.: Chem. Soc., 22 174–185 (1869)). Later, many reports were presented on fluorescence quenching of polycyclic aromatic compounds by oxygen or sulfur dioxide and the analysis of these chemical species utilizing fluorescence quenching. However, few reports have been presented on the fluorescent dye for chloride ion determination by fluorescence quenching. For halide ion analysis, 6-methoxy-1-(3-sulfopropyl)quinolinium, and tetrafluoroborate salt of 3-(10-methylacridinium-9-yl)propionic acid were reported as the fluorescent dye (Urbano, E., et al: Anal. Chem., 56 427 (1984)).

Generally, florescence quenching by halide ion including chloride ion follows Stern-Volmer equation (Wolfbeis, et al.: Anal. Chem., 1985, 57, 2551–2561). At a certain halogen ion concentration, the larger the quenching constant of a fluorescent dye, the more is the decrease of the fluorescence intensity of the dye. Therefore, a fluorescent dye having a larger quenching constant enables halogen ion determination with higher sensitivity. The quenching constants of organic fluorescent dyes to chloride ion are generally lower than $1M^{-1}$. However, the above two fluorescent dyes have respectively a quenching constant of 1 to $10M^{-1}$ to chloride ion, and are useful for high-sensitive determination of chloride ion.

For the determination of chloride ion according to fluorescence quenching, bromide ion and iodide ion interfere with the analysis since halogen ion having a larger atomic weight causes stronger quenching. Accordingly, for the measurement of chloride ion concentration, a fluorescent dye is demanded which has a larger quenching constant to chloride ion, and has small quenching constants to bromide ion and iodide ion.

The analytical method utilizing fluorescent quenching by chloride ion is based on decrease of a fluorescence intensity as a function of chloride ion concentration, and the chloride ion concentration is determined indirectly from the change of the fluorescence intensity. Many organic and inorganic fluorescent dyes are available whose fluorescence is quenched by chloride ion. A fluorescent dye which has a large quenching constant to chloride ion enables selective determination of chloride ion.

Fluorescence of the dyes which have been reported hitherto for determination of chloride ion are strongly quenched also by other coexisting halogen ions, in particular, by iodide ion, and are not applicable to the precise determination of chloride ion in a sample containing another halide ions.

As a sensor for chloride ion, an electrochemical sensor, namely a chloride ion-selective electrode is employed. Ion-selective electrodes, which are readily handleable and highly sensitive, are widely useful as analysis for a sample collected into a beaker or a like container. However, the ion-selective electrode has a high electrical impedance. Therefore, the sensor is required to be placed at a site nearest to the signal measurement instrument, (i.e., a potentiometer). Remote-sensing with the ion-selective electrode set at the measurement site is not practicable.

Accordingly, the ion-selective electrode, when it is used in continuous in situ analysis, has to be placed together with the potentiometer in the measurement site. The ion-selective electrode comprises a working electrode and a reference electrode. The reference electrode could not readily be miniaturized. Therefore, few instances have been found in which the ion-selective electrode is used directly in a living body. Further, the ion-selective electrode is limited in practical use since it is not readily handleable because of the fragile portion thereof, and the measurement is strongly interfered by pH and coexisting ions in the sample.

Recently, a sensor has been disclosed which is useful for remote-sensing and can be made in a minute size, comprising a sensing membrane having an analysis reagent immobilized thereon and an optical waveguide such as optical fiber in combination (Widmer, H. M.: Anal. Method Instrum., 1 60–72 (1993)). This sensor has a sensing membrane which comprises a support such as a polymer membrane and an analytical reagent immobilized on the support and responsive optically to an object compound. The sensing membrane is immersed in a sample solution to detect an optical change (e.g., absorbance change, and fluorescent intensity change) of the immobilized analytical reagent, thereby obtaining the concentration of the chemical interested.

An optical change of an analytical reagent may be measured by setting a sensing membrane directly onto a wall of a cell of a spectrophotometer or a fluorometer, or by connecting the sensing membrane to the photometer through an optical fiber. Since the analytical reagent is fixed on the sensing membrane, it enables continuous measurement without consuming the reagent. Since the sensing membrane with a size of less than 1 mm$^2$ enables detection of an optical change sufficiently, the sensor can be made in a minute size.

An optical change of a sensing membrane can be detected with a measurement apparatus connected to the sensitive membrane through an optical fiber, thereby remote-sensing being readily practiced by utilizing the optical fiber.

Analysis of chloride ion with high precision is usually conducted by a batch treatment. In the batch treatment, a sample is pretreated, an indicator reagent or a color reagent is added thereto, and the chloride ion concentration is measured by titrimetry or colorimetry. However, the analytical method with the batch treatment is not applicable to continuous measurement of chloride ion as mentioned above.

Accordingly, a sensor is demanded which is capable of detecting chloride ion without preparation and pretreatment of samples, and which is applicable to remote-sensing for in situ measurement of chloride ion in river water and other environmental water, chemical solutions in industrial plants, industrial waste water, and the like. Further, a microsensor is demanded for in vivo measurement by inserting a sensor into a living body without damaging the living body.

The chemical composition of samples is usually complicated, and coexisting ions and organic compounds may affect greatly the analytical results. Therefore, a sensor for chloride ion is demanded which is little affected by coexisting substances. In particular, sensing of chloride ion with high precision in the presence of other halide ions is indispensable in production of high-purity reagents such as chlorine and metal chlorides for use of semiconductor production.

SUMMARY OF THE INVENTION

The present invention intends to provide a fluorescent dye for detecting chloride ion selectively by fluorescence quenching, even in the presence of an interfering species such as iodide ion, and to provide a continuous analytical method of chloride ion by use of the fluorescent dye.

The present invention also intends to provide a chemical sensor for an optical measurement of a chloride ion concentration with high sensitivity.

The present invention further intends to provide a chemical sensor for an optical measurement of a low concentration of chloride ion with high sensitivity.

The above objects can be achieved by the present invention.

According to the present invention, there is provided a fluorometric analysis for detecting chloride ion in a sample by fluorescence quenching of a fluorescent dye, the fluorescent dye being selected from the group consisting of 3,6-bis(dimethylamino)acridine and a derivative thereof of the formulae

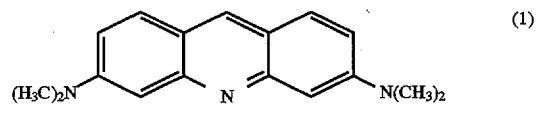

and

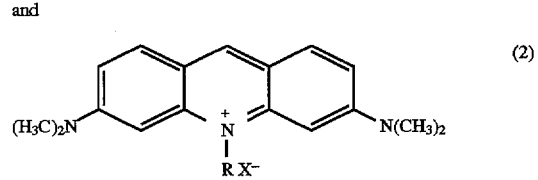

wherein R is alkyl having 1 to 30 carbon atoms, and $X^-$ is a halogen ion.

According to the present invention, there is further provided a chemical sensor for measuring a chloride ion concentration employing a dye composed of 3,6bis(dimethylamino)-10-alkylacridinium halide of the formula

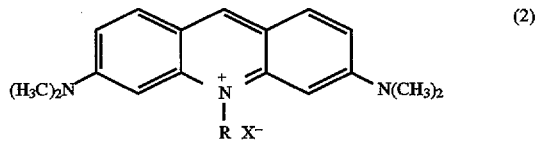

wherein R is alkyl having 1 to 30 carbon atoms, and $X^-$ is a halogen ion.

According to the present invention, there is still provided a chemical sensor for measuring a chloride ion concentration comprising a support having a fluorescent dye immobilized thereon, and a chloride ion concentrating means bonded to the support, the fluorescent dye being 3,6bis (dimethylamino)-10-alkylacridinium halide of the formula

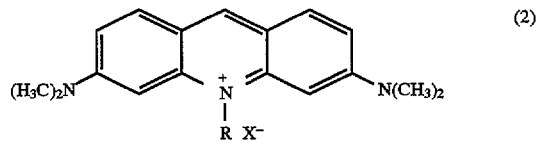

wherein R is alkyl having 1 to 30 carbon atoms, and $X^-$ is a halogen ion.

BRIEF DESCRIPTION OF THE DRAWINGS

FIG. 6A shows the whole construction including an optical system and a measurement system. FIG. 6B is an enlarged view of a portion of the sensor.

FIGS. 8A and 8B show a construction of another embodiment of the present invention. FIG. 8A shows the whole construction including an optical system and a measurement system. FIG. 8B is an enlarged view of a portion of the sensor.

FIG. 9 shows a construction of still another embodiment of the present invention.

DESCRIPTION OF PREFERRED EMBODIMENTS

Figure 1:
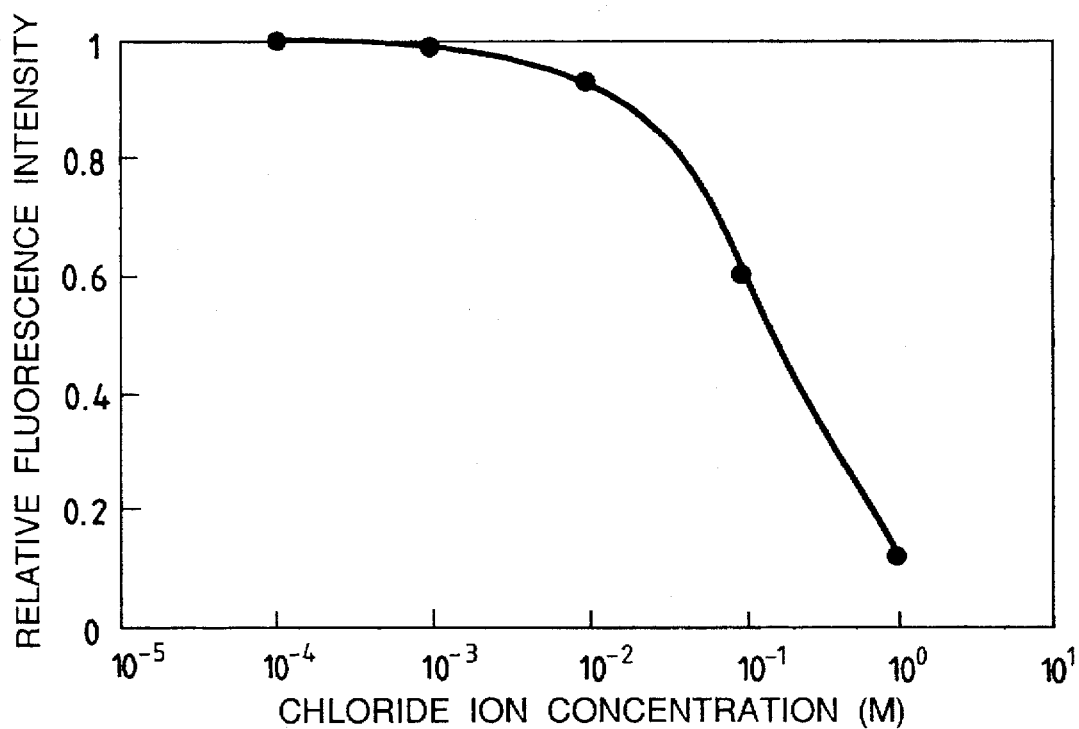
FIG. 1 is a graph showing dependency of a relative fluorescence intensity on a chloride ion concentration of the solution in Example 1.

Fluorescence quenching by a halogen ion such as chloride ion is based on transfer of excitation energy of an optically excited fluorescent dye to the halogen ion to relax the fluorescent dye to the ground state without emitting fluorescence.

In an analysis of the chloride ion, a fluorescent dye is dissolved in a prescribed concentration in the sample solution preliminarily or immediately before the analysis, and then the fluorescence intensity is measured. Separately, the fluorescence intensity of the fluorescent dye solution is measured at the prescribed concentration of the fluorescent dye in the absence of the chloride ion. The chloride ion concentration is obtained from the fluorescence intensities in the absence and presence of the chloride ion.

When direct addition of the fluorescent dye into the sample solution is impracticable owing to diffusion, flowing-out, or toxicity of the fluorescent dye, the fluorescent dye is immobilized onto a suitable support through the substituent at the 10-position of 3,6-bis(dimethylamino)-10-alkylacridinium ion, and this support is brought into contact with the sample solution to measure the chloride ion concentration from the fluorescent intensity. With this method, the fluorescent dye can be recovered entirely with the support after the analysis without consumption of the fluorescent dye.

For example, the fluorescence characteristics (e.g., fluorescence intensity, excitation wavelength, and fluorescence wavelength) of 3,6-bis(dimethylamino)-10-alkylacridinium ion depends little on the chain length of the alkyl group at 10-position. Therefore, a suitable alkyl group, preferably having 1 to 30 carbon atoms, is introduced to the 10-position, and the fluorescent dye is immobilized physically to a support by utilizing the hydrophobicity of the alkyl chain.

The alkyl group at 10-position of 3,6-bis(dimethylamino)-10-alkylacridinium ion may have a substituent including a halogen atom, a sulfonate group, an amino group, a styryl group, a nitro group, a hydroxyl group, a carboxyl group, a ketone group, a cyano group, a substituted or unsubstituted tertiary or quaternary alkyl group, a substituted or unsubstituted aryl group, and a substituted or unsubstituted cycloalkyl group.

The above alkyl group may be modified with a reactive group such as a maleimide group and a succinoimide group. The fluorescent dye modified with the reactive group can be fixed to a compound or a surface of a support having a functional group such as —SH or the like, and the support having the chemically fixed fluorescent dye is also useful for the analysis.

The support for immobilizing the fluorescent dye includes particles used for chromatography, polymeric compounds to be used for functional membranes, and gel-like materials. More specifically, the support is exemplified by particles such as porous glass, zeolite, silica gel, and alumina; ion exchange resins; polymeric compounds such as polymethyl methacrylate, polyvinyl chloride, and polyurethane; and gel-like materials such as polyvinyl alcohol, polyacrylamide and the like.

The counter anion to 3,6-bis(dimethylamino)-10-alkylacridinium cation includes halogen ions such as bromide ion and chloride ion, hydroxide ion, thiocyanate ion, borate ion, and perchlorate ion and the like.

The fluorometric analysis of the present invention is suitable for measurement of chloride ion in starting materials, intermediate products, and final products of chemicals. The fluorometric analysis is also useful for a chloride ion measurement of cooling water and waste water in industrial plants, environmental water such as underground water and river water, and biological sample such as blood and intracellular fluid. In particular, a chloride ion concentration is continuously monitored without consuming the fluorescent dye; a support having a fluorescent dye immobilized thereon is immersed in a flow of a sample liquid sent by a pump and the fluorescence intensity is measured.

A sample to be tested is desirably an aqueous solution, but may contain a water-soluble solvent such as ethanol and acetonitrile. The sample solution has preferably a pH in a neutral range. However, the analysis is practicable over a wide pH region, since the fluorescent characteristics of 3,6-bis(dimethylamino)-10-alkylacridinium ion are nearly constant in the pH range of from 3 to 11. Furthermore, the method of the present invention is applied to samples in a wide range of ionic strength, since the fluorescent characteristics of 3,6-bis(dimethylamino)-10-alkylacridinium ion depend little on ionic strength. The above-mentioned fluorescent characteristics of the fluorescent dye render unnecessary the pretreatment of the sample such as pH adjustment and ionic strength adjustment in the analysis, and provide a continuous in situ measurement of a variety of samples.

The excitation light source for measurement of the fluorescence of 3,6-bis(dimethylamino)acridine and its derivatives includes tungsten lamp or xenon lamp spectrally separated by a filter or a diffraction grating, and light-emitting diode. The 3,6-bis(dimethylamino)acridine and its derivatives have a maximum excitation wavelength at near 490 nm, which coincides well with the light wavelength of commercial argon-ion laser (488 nm). Therefore, the laser may be used as the excitation light source. In particular, when a sufficient amount of the fluorescent dye cannot be added to a sample, or when the amount of the fluorescent dye immobilized on a support is insufficient, a sufficient fluorescence intensity is not obtained for the analysis. In such cases, the fluorescence can be measured sensitively by using a laser as the excitation light source to obtain a chloride ion concentration with a high precision. The fluorescence from the fluorescent dye is separated by a filter or a diffraction grating from the excitation light, and the fluorescence intensity is measured by a photodiode, photomultiplier, or a CCD camera.

The fluorometric analysis employing the dye of the present invention is useful not only for simple measurement of chloride ion concentration, but also for analysis of a chemical species which is in a stoichiometric relation with chloride ion in a chloride ion-participating reaction. For example, in a reaction of chlorine addition to, or chlorine elimination from an organic compound, the amount of the starting organic compound or of the reaction product can be indirectly obtained from the chloride ion concentration measured by the analysis method of the present invention.

Next, a sensor employing the analysis method of the present invention is described below.

A sensitive membrane having 3,6-bis(dimethylamino)-10-alkylacridinium ion immobilized thereon is set onto an internal wall of a transparent sample cell made of glass or quartz. The cell is filled with a sample solution, and the intensity of fluorescence from the sensitive membrane is measured by means of fluorometer. The chloride ion concentration is obtained by comparing the measured value with the fluorescence intensity in the absence of the chloride ion. Analysis of many samples is conducted without consuming the dye by replacing the sample solution in the cell successively.

In another way, the sensing membrane is set in a flow type cell, and the chloride concentration in the sample solution flowing in the cell is measured continuously. In still another way, an optical sensor for remote-sensing is prepared by placing the sensitive membrane in an optical waveguide such as optical fiber. More specifically, a sensitive membrane is set at the end of an optical fiber, and the fluorescence intensity is measured at the other end of the optical fiber. With this optical sensor, continuous remote-sensing of chloride ion concentration is achieved within the distance range in which optical signals are transmittable through the optical fiber. The optical waveguide includes optical fibers made from glass, quartz, or plastics, and plate-shaped waveguides made from a similar material.

A low concentration of chloride ion can be measured in the present invention by employing the fluorescent dye-implanting support in combination with a chloride ion-concentrating means. Thereby, the chloride ion is concentrated and sufficient quenching is observced, which enables measurement of a chloride ion concentration with high sensitivity even with an inexpensive photometer.

The chloride ion-concentrating means in the present invention may be an ion-exchange membrane, preferably, an anion exchange membrane. The anion-exchange membrane selectively adsorbs anion and increases the chloride ion concentration in the vicinity of the support immobilizing the fluorescent dye to intensify the quenching. Thereby, quantitative measurement of the chloride ion concentration is feasible, since the amount of the chloride ion adsorbed is proportional to the chloride ion concentration in the sample medium. The ion concentration in the anion-exchange membrane is in equilibrium with that in the vicinity. Increase of the concentration of the ion in the vicinity causes adsorption of the ion by the membrane, whereas decrease of the concentration of the ion causes desorption of the ion, whereby continuous measurement of the concentration is achieved.

The optical sensor according to the present invention is useful for the measurement of chloride ion in starting materials, intermediate products and final products of synthesized chemicals. It is also useful for analysis of cooling water and waste water in industrial plants. It is further useful for sensing of chloride ion in environmental water such as underground water and river water, and in biological samples such as blood and intracellular fluid.

The sensor of the present invention is useful not only for simple measurement of chloride ion concentration, but also for analysis of a chemical species which is in a stoichiometric relation with chloride ion in a chloride ion-participating reaction. For example, in a chlorine addition to, or chlorine elimination from an organic compound, the amount of the starting organic compound or of the reaction product can be indirectly obtained from the measurement result of chloride ion concentration measured by the analysis method with the sensor of the present invention.

The present invention is described more specifically without limiting the invention in any way.

EXAMPLE 1

[Fluorescence quenching of 3,6-bis(dimethylamino)-10-dodecylacridinium bromide by chloride ion]

(1) A 0.1M potassium phosphate buffer solution (pH=7.0) was prepared which contained 1 µM 3,6-bis(dimethylamino)-10-dodecylacrydinium bromide (commercial product). Therein, potassium chloride was dissolved so as to prepare sample solutions of a predetermined concentration ($10^{-4}$ to $10^{0}$M).

(2) The fluorescence intensities of the above solutions were measured at the excitation wavelength of 490 nm and the fluorescence wavelength of 530 nm. The relative fluorescence intensities were obtained by taking the fluorescence intensity in the absence of chloride ion to be 1.00.

The results are shown in FIG. 1. The Stern-Volmer equation for fluorescence quenching is $$F/F_0 = (1 + k[Cl])^{-1}$$

where F is a fluorescence intensity in the presence of chloride ion, $F_0$ is a fluorescence intensity in the absence of chloride ion, k is a quenching constant, and [Cl] is a chloride ion concentration.

From FIG. 1 and the above Stern-Volmer equation, the quenching constant was $6.7M^{-1}$.

Comparative Example 1

[Quenching of fluorescence of 6-methoxy-1-(3-sulfopropyl)quinolinium, and tetrafluoroborate salt of 3-(10-methylacridinium-9-yl)propionic acid by chloride ion]

(1) 0.1M potassium phosphate buffer solutions (pH=7.0) were prepared which contained respectively 1 µM 6-methoxy-1-(3-sulfopropyl)quinolinium, or 1 µM tetrafluoroborate salt of 3-(10-methylacridinium-9-yl)propionic acid. To the fractions of the above solutions, potassium chloride was dissolved so as to prepare sample solutions of a predetermined concentration ($10^{-4}$ to $10^{0}$M).

(2) The fluorescence intensities of the above solutions were measured at the excitation wavelength and the fluorescence wavelength shown in Table 1. The relative fluorescence intensities were obtained by taking the fluorescence intensity in the absence of chloride ion to be 1.00.

| Fluorescent dye | Excitation wavelength | Fluorescence wavelength |
| --- | --- | --- |
| 3,6-bis(dimethylamino)-10-dodecylacridinium bromide | 490 nm | 530 nm |
| 6-methoxy-1-(3-sulfopropyl)- | 320 nm | 440 nm |

| Fluorescent dye | Excitation wavelength | Fluorescence wavelength |
| --- | --- | --- |
| quinolinium 3-(10-methylacridinium-9-yl)propionic acid | 360 nm | 490 nm |

The quenching constants (k) according to Stern-Volmer equation were $7.6M^{-1}$ for 6-methoxy-1-(3-sulfopropyl) quinolinium, and $9.3M^{-1}$ for 3-(10-methylacridinium-9-yl) propionic acid.

Thereby, 3,6-bis(dimethylamino)-10-dodecylacridinium ion was found to have a large quenching constant comparable to the above fluorescent dyes.

EXAMPLE 2

[Fluorescence quenching of 3,6-bis(dimethylamino) acridine and 3,6-bis(dimethylamino)-10-hexadecylacridinium bromide by chloride ion]

(1) 0.1M potassium phosphate buffer solutions (pH=7.0) were prepared which contained 1 µM 3,6-bis (dimethylamino)acridine (commercial product) or 1 µM 3,6-bis(dimethylamino)-10-hexadecylacridinium bromide (synthesized according to Kawabata, Y. et al.: Anal. Chem., 62 2054–2055 (1990)). Into the fractions of the above solutions, potassium chloride was dissolved so as to prepare sample solutions of a predetermined concentration ($10^{-4}$ to $10^0$M).

(2) The fluorescence intensities of the above solutions were measured at the excitation wavelength of 490 nm and the fluorescence wavelength of 530 nm. The quenching constants for chloride ion were calculated to be $7.3M^{-1}$ for 3,6-bis(dimethylamino)-acridine, and $6.4M^{-1}$ for 3,6-bis (dimethylamino)-10-hexadecylacridinium bromide.

Thereby, 3,6-bis(dimethylamino)-acridine, and the derivative thereof having an alkyl substituent at 10-position were found to have a high quenching constants for chloride ion.

EXAMPLE 3

[Interference of iodide ion in fluorometric analysis of chloride ion]

(1) 0.1M potassium phosphate buffer solutions (pH=7.0) were prepared which contained respectively 1 µM 3,6-bis (dimethylamino)-10-dodecylacridinium bromide, 1 µM 6-methoxy-1-(3-sulfopropyl)quinolinium, or 1 µM tetrafluoroborate salt of 3-(10-methylacridinium-9-yl)propionic acid. To each of the fractions of the above solutions, potassium iodide was dissolved in a concentration of 1 mM, and potassium chloride was dissolved so as to prepare sample solutions of a predetermined concentration ($10^{-4}$ to $10^0$M).

(2) The fluorescence intensities of the above solutions were measured, and the relative intensities were obtained by taking the fluorescent intensity in the absence of chloride ion to be 1.00 at the same excitation wavelength and the fluorescence wavelength as in Comparative Example 1.

(3) The interference of the iodide ion was examined from the difference of the relative fluorescence intensities in the absence of iodide ion (FIG. 1) from those in the presence of the iodide ion.

Figure 2:
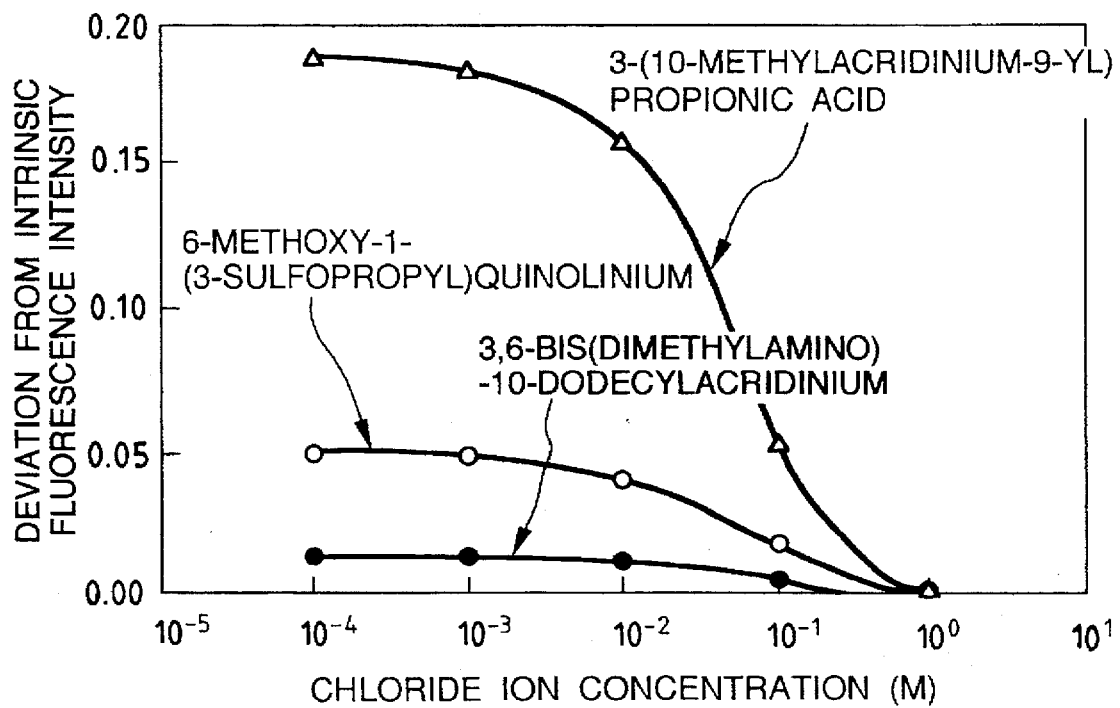
FIG. 2 is a graph showing dependency of the deviation from the intrinsic fluorescence intensity caused by the interference of iodine ion in Example 3.

The results are shown in FIG. 2 wherein the ordinate shows the deviation of the relative fluorescence intensities in the presence of the iodide ion from those in the absence of the iodide ion (intrinsic fluorescence intensities), and the abscissa shows the concentration of the chloride ion.

From FIG. 2, it was confirmed that the fluorometric analysis of chloride ion concentration with 3,6-bis (dimethylamino)-10-dodecylacridinium is less interfered by iodide ion in comparison with the analysis with conventional fluorescent dyes.

Further, the same experiment was conducted with 3,6-bis (dimethylamino)acridine, and 3,6-bis(dimethylamino)-10-hexadecylacridinium bromide as the fluorescent dye, and it was also confirmed that the analysis with these fluorescent dyes is interfered very little by iodide ion.

EXAMPLE 4

[Preparation of sensitive membrane and sensing of chloride ion with fluorophotometer]

(A) 3 Grams of acrylamide, 58 mg of N,N'-methylenebis (acrylamide), 2.7 mg of riboflavin, and 2.7 mg of ammonium peroxodisulfate were dissolved in 25 ml of a 0.1M phosphate buffer solution (pH=7.0), and thereto 3 g of an aqueous 10% solution of polyacrylamide (average molecular weight: $7\times10^5$) was added.

2 Milliliters of this solution was placed in a Petri dish of 70 mm diameter, and photopolymerization was achieved by light irradiation of a tungsten lamp with 300 W output. Then the resulting polymer membrane was dipped in an aqueous solution of 3,6-bis(dimethylamino)-10-dodecylacridinium bromide (concentration: $10^{-5}$M, R: $-C_{10}H_{21}$, $X^-$: $Br^-$ in the formula (2)) to immobilize this fluorescent dye thereon to prepare a sensing membrane.

(B) The sensitive membrane was set on an internal wall of a triangular-type fluorometric cell. Potassium chloride solutions of a prescribed concentration ($10^{-4}$ to $10^{-1}$M) were prepared using a 0.1M phosphate buffer solution (pH: 7.0). A fraction of one of the potassium chloride solutions was filled into the aforementioned cell. Fluorescence intensity was measured at an excitation wavelength of 490 nm and fluorescence wavelength of 530 nm, and the relative fluorescence intensity was obtained by taking the fluorescence intensity in the absence of chloride ion as 1.00. Then, the potassium chloride solution in the cell was discarded, and the inside of the cell was washed with the buffer solution. Each potassium chloride solution of different concentrations was filled into the cell, and the relative fluorescence intensity was obtained.

Figure 3:
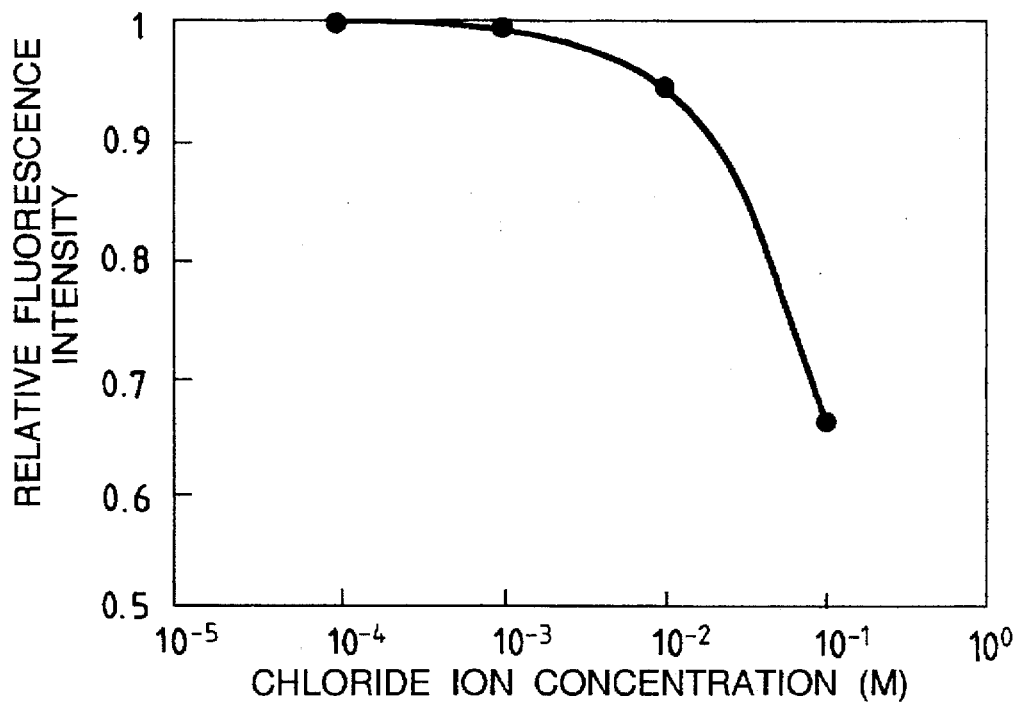
FIG. 3 shows dependency of a relative fluorescence intensity on a chloride ion concentration on the sensitive membrane in Example 3.

The results are shown in FIG. 3. From FIG. 3, it was confirmed that the use of the sensing membrane enabled the repetitive measurement of the chloride ion concentration at high sensitivity without consuming the fluorescent dye. The sensitivity to chloride ion concentration of the sensing membrane having the dye fixed thereon was dropped by about 20% or less in comparison with the sensitivity in measurement by use of a solution of the fluorescent dye. This would result from increase of the background caused by scattering of the excitation light at the wall of the fluorometric cell.

EXAMPLE 5

[Measurement of chloride ion by optical fiber type sensor]

(A) 3 Grams of acrylamide, 58 mg of N,N'-methylenebis (acrylamide), 2.7 mg of riboflavin, and 2.7 mg of ammonium peroxodisulfate were dissolved in 25 ml of a 0.1M phosphate buffer solution (pH=7.0), and thereto 3 g of an aqueous 10% solution of polyacrylamide (average molecular weight: $7\times10^5$) was added.

Into this solution, was dipped one end of an optical fiber made from quartz and having a core diameter of 100 μm and a cladding diameter of 140 μm, and was taken out. The drop of the solution remained on the tip of the optical fiber was photo-polymerized by light irradiation of a tungsten lamp with 300 W output. Then the resulting polymer membrane was immersed in an aqueous solution of 3,6-bis(dimethylamino)-10-dodecylacridinium bromide (concentration: $10^{-5}$M, R: —$C_{10}H_{21}$, $X^-$: $Br^-$ in the formula (2)) to immobilize this fluorescent dye thereon to prepare an optical fiber type sensor.

(B) Potassium chloride solutions of a prescribed concentration ($10^{-4}$ to $10^{-1}$M) were prepared using a 0.1M phosphate buffer solution (pH: 7.0). The sensor was dipped into a fraction of one of the potassium chloride solutions. Argon-ion laser light (wavelength: 488 nm, output: 10 μW) was introduced to the end of the optical fiber, and the fluorescence intensity was measured from the other end of the optical fiber at a fluorescence wavelength of 530 nm. The relative fluorescence intensity was obtained by taking the fluorescence intensity in the absence of chloride ion as 1.00. This operation was repeated successively for the respective potassium chloride solutions.

Figure 4:
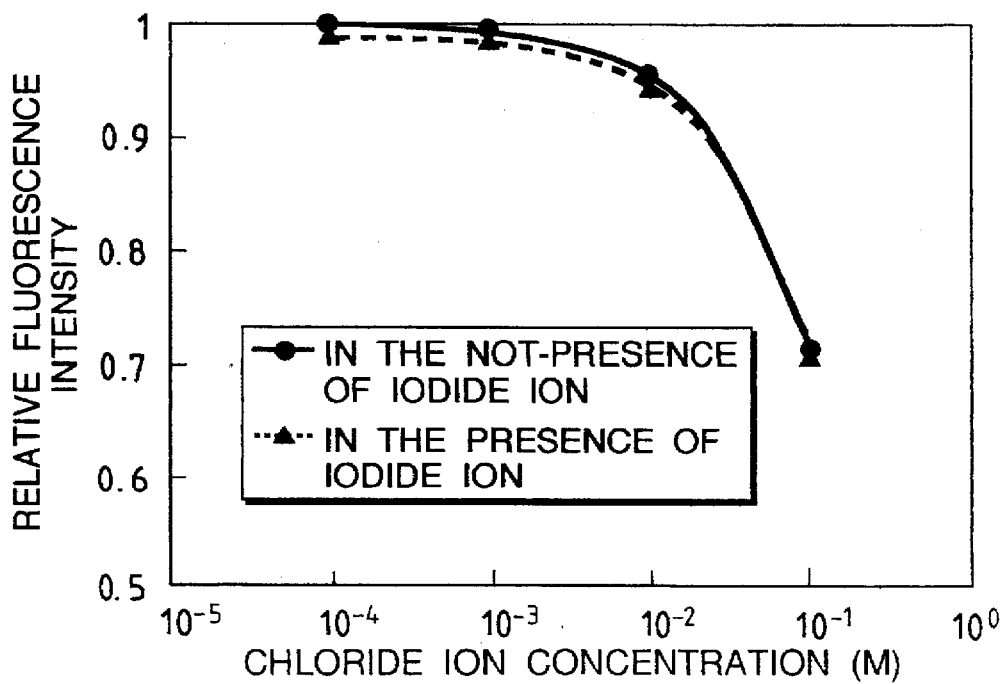
FIG. 4 shows dependency of a relative fluorescence intensity on a chloride ion concentration on the sensitive membrane in Examples 5 and 6.

The results are shown in FIG. 4. From FIG. 4, it was confirmed that the use of this optical sensor enabled continuous measurement of the chloride ion concentration. The sensitivity to a chloride ion concentration of the optical sensor was dropped by about 30% or less in comparison with the sensitivity in measurement by use of a solution of the fluorescent dye. This would result from increase of the background caused by scattering of the excitation light at the both end surfaces of the optical fiber.

EXAMPLE 6

[Interference of iodide ion in sensing of chloride ion]

(A) 3 Grams of acrylamide, 58 mg of N,N'-methylenebis(acrylamide), 2.7 mg of riboflavin, and 2.7 mg of ammonium peroxodisulfate were dissolved in 25 ml of a 0.1M phosphate buffer solution (pH=7.0), and thereto 3 g of an aqueous 10% solution of polyacrylamide (average molecular weight: $7 \times 10^5$) was added.

Into this solution, was dipped one end of an optical fiber made from quartz and having a core diameter of 100 μm, and a cladding diameter of 140 μm, and was taken out. The drop of the solution remained on the tip of the optical fiber was photo-polymerized by light irradiation of a tungsten lamp with 300 W output. Then the resulting polymer membrane was immersed in an aqueous solution of 3,6-bis(dimethylamino)-10-dodecylacridinium bromide (concentration: $10^{-5}$M, R: —$C_{10}H_{21}$, $X^-$: $Br^-$ in the formula (2)) to immobilize this fluorescent dye thereon to prepare an optical fiber type sensor.

(B) Potassium chloride solutions of a prescribed chloride ion concentration ($10^{-4}$ to $10^{-1}$M) containing potassium iodide in a concentration of 1 mM were prepared using a 0.1M phosphate buffer solution (pH: 7.0). The sensor was dipped into a fraction of one of the potassium chloride solutions, and the relative fluorescence intensity was measured in the same manner as in Example 5 to examine the interference of iodide ion.

The results are shown in FIG. 4. From FIG. 4, it was confirmed that the optical sensor was capable for determining chloride ion selectively with little interference by iodide ion.

EXAMPLE 7

[Measurement of chloride ion concentration by planar substrate type sensor]

(A) 3 Grams of acrylamide, 58 mg of N,N'-methylenebis(acrylamide), 2.7 mg of riboflavin, and 2.7 mg of ammonium peroxodisulfate were dissolved in 25 ml of a 0.1M phosphate buffer solution (pH=7.0), and thereto 3 g of an aqueous 10% solution of polyacrylamide (average molecular weight: $7 \times 10^5$) was added.

The above solution was dropped on a planar substrate (material: BK 7, 10 mm square, and 1 mm thick) having an aluminum thin film on the back face thereof, and the above solution was spreaded thin. Then the solution was irradiated with light of a tungsten lamp with 300 W output. Then, the resulting polymer membrane was immersed in an aqueous solution of 3,6-bis(dimethylamino)-10-dodecylacridinium bromide (concentration: $10^{-5}$M, R: —$C_{10}H_{21}$, $X^-$: $Br^-$ in the formula (2)) to immobilize this fluorescent dye thereon to prepare a planar substrate type sensor.

(B) Potassium chloride solutions of a prescribed chloride ion concentration ($10^{-4}$ to $10^{-1}$M) were prepared using a 0.1M phosphate buffer solution (pH: 7.0). The sensor was dipped into a fraction of one of the potassium chloride solutions. Argon-ion laser light (wavelength: 488 nm, output: 10 μW) was introduced into the planar substrate from a lateral face thereof (thickness side) to cause total reflection of the laser light in the substrate, and the fluorescent dye in the polymer membrane was excited by evanescent light generated on the substrate surface. The evanescent fluorescence intensity was measured at the fluorescence wavelength of 530 nm from the side of planar substrate. The relative fluorescence intensity was obtained taking the fluorescence intensity in the absence of chloride ion to be 1.00. This procedure was repeated successively for the respective potassium chloride solutions.

Figure 5:
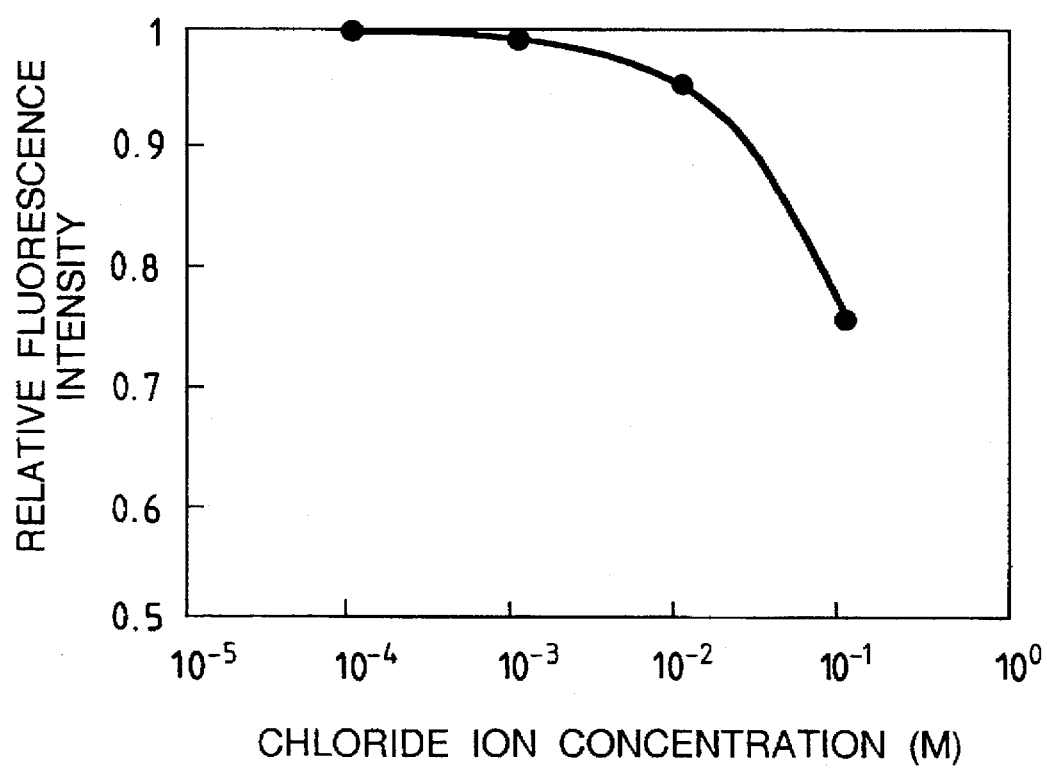
FIG. 5 shows dependency of a relative fluorescence intensity on a chloride ion concentration on the sensitive membrane in Example 7.

The results are shown in FIG. 5. From FIG. 5, it was confirmed that the use of this optical sensor enabled continuous and sensitive measurement of the chloride ion concentration. The sensitivity to chloride ion concentration of this optical sensor was dropped by about 50% or less in comparison with the sensitivity in measurement by use of a solution of the fluorescent dye. This would result from low efficiency of the evanescent light in exciting the fluorescent dye and increase of the background due to measurement of fluorescent in a propagating direction of the exciting light.

EXAMPLE 8

Figure 6A:
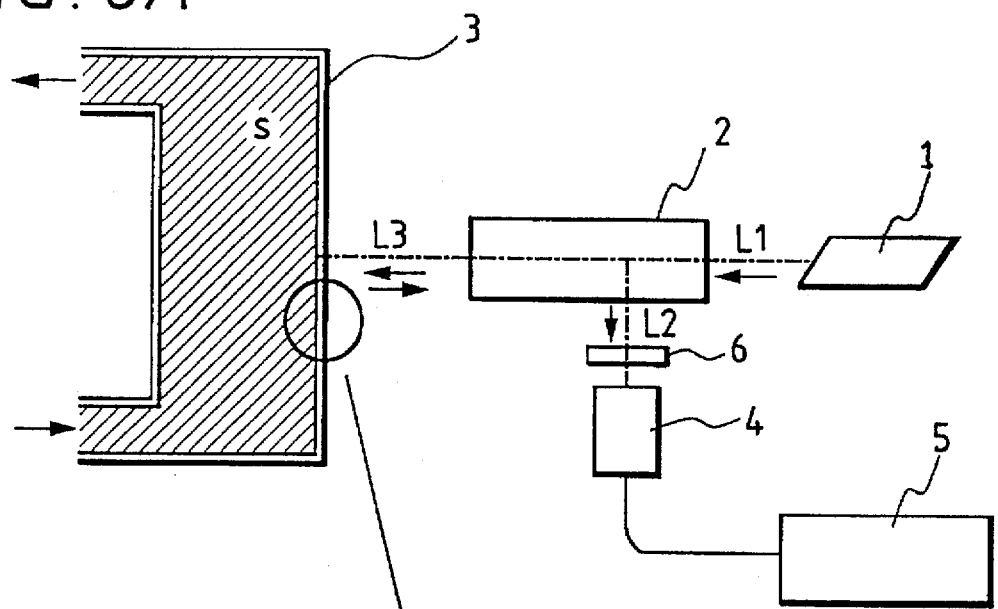
FIGS. 6A and 6B show a construction of an embodiment of the present invention.
Figure 6B:
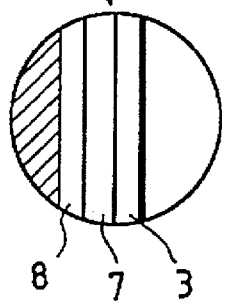

FIGS. 6A and 6B show an example of constitution of an embodiment of the present invention. In an optical path L1 for an exciting light source 1 and another optical path L2 for a light detector 4, an optical system 2 was provided for mixing the light beams of the optical paths L1, L2 into an optical path L3. A flow cell 3 was placed in the optical path L3, and a sample solution s was filled in the flow cell. In front of the light detector 4, a band-pass filter 6 was placed. The output of the light detector was connected to a signal processing means 5. On the internal wall of the flow cell 3, a sensing membrane 7 on which a fluorescent dye composed of 3,6-bis(dimethylamino)-10-alkylacrtdinium halide was immobilized. Further on the sensing membrane 7, an ion-exchange membrane 8 was bonded as the chloride ion concentrating means. Therefore, the wall of the flow cell 3 was constituted of three layers (FIG. 6B).

The fluorescent dye composed of 3,6-bis(dimethylamino)-10-alkylacridinium halide has maximum excitation wavelength around 490 nm and emits strong fluorescent light around 530 nm, and the presence of chloride ion decreases the fluorescence intensity selectively.

The sensitive membrane 7, which was a polyacrylamide membrane in this Example, was prepared by photopolymerization. For preparation of the polyacrylamide membrane, a solution was prepared by dissolving 3 g of acrylamide, 58 mg of N,N'-methylenebis(acrylamide), 2.7 mg of riboflavin, and 2.7 mg, of ammonium peroxodisulfate in 25 ml of a 0.1M phosphate buffer solution (pH=7.0), and adding thereto 3 g of an aqueous 10% solution of polyacrylamide (average molecular weight: $7 \times 10^5$). In the flow cell 3, 0.1 ml of the above solution was placed and the solution was exposed to light from a tungsten lamp (output: 300 W) to cause photopolymerization. The 3,6-bis(dimethylamino)-10-alkylacridinium halide in this Example was 6,6-bis (dimethylamino)-10-dodecylacridinium bromide. It was immobilized on the above photopolymerized membrane by immersing the membrane into an aqueous solution of the acridinium ion (concentration: $10^{-5}$M), whereby the acridinium ion was immobilized on the membrane in an amount of $1 \times 10^{-6}$ mol/m$^2$. The polymerized film was formed directly in the flow cell in this Example. In another way, the fluorescent dye may be immobilized on a separately polymerized film and be fixed in a cell.

On the above sensitive film 7, an ion-exchange membrane 8 (TASN-17, produced by Tosoh Corporation, 0.2 mm thick) was overlaid and fixed.

Figure 7:
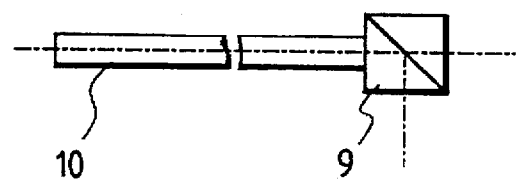
FIG. 7 illustrates a construction of an optical system useful for the present invention.

The excitation light source 1 employed is an argon-ion laser with 488 nm emission. Instead, LED, or a combination of a halogen lamp with a band-pass filter may be employed. The photodetector 4 is preferably a photomultiplier tube, but may be an avalanche photodiode, or a photodiode. The band-pass filter 6 placed before the photodetector 4 transmits light in the wavelength range of 530±10 nm. The optical system 2 is preferably a combination of a beam splitter 9 and an optical fiber 10 as shown in FIG. 7 in view of simplicity.

The excitation light emitted from the excitation light source 1 passed through the optical system 2, penetrated through the wall of the flow cell 3, and reached the sensitive membrane 7. Thereby, the fluorescent dye in the sensing membrane 7 was excited to emit fluorescence. The fluorescence penetrates the wall of the flow cell 3, passed through the optical system 2, and was detected by the photodetector 4. The signal from the photodetector was processed by the signal processing means 5.

The photodetector 4 employed was a photomultiplier tube, and the signal processing means 5 employed was an electric circuit constituted from an AD converter, a memory, a microcomputer, and so forth.

The fluorescence intensity in the absence of chloride ion in the sample solution s is represented herein by $I_0$. When chloride ion is contained in the sample solution s, the chloride ion is attracted by the ion-exchange membrane 8 to increase chloride ion concentration around the sensitive membrane 7 to increase the degree of fluorescence quenching even when the chloride ion concentration is low. Therefore the fluorescence intensity $I_1$ in the presence of chloride ion is lower than $I_0$. The difference between $I_1$ and $I_0$ is a function of the chloride ion concentration. By memorizing the function in the signal processing means, the chloride ion concentration can be determined from the fluorescence intensity according to the memory. Continuous measurement of the chloride ion concentration is achieved when the sample solution s is in a flowing state.

Although the flow cell is used for continuous measurement in this Example, other types of cell may be used, for example, a standard analytical cell.

The optical system 2 may be omitted. In this case the excitation light source 1 and the photodetector 4 are arranged such that the optical path L2 of the photodetector 4 is oriented at an angle Θ (Θ≠0) to the optical path L1 of the excitation light source 1.

The sensor in this Example was capable of measuring a chloride ion concentration to as low as $10^{-3}$ M with satisfactory reproducibility and selectivity even in coexistence of other halogen ion.

EXAMPLE 9

FIG. 8A illustrates a constitution of another embodiment of the present invention. FIG. 8B is an enlarged view of a tip of the optical fiber in FIG. 8A. An end of an optical fiber 11 (made from quartz, core diameter: 100 μm, cladding diameter: 140 μm) was connected to a main body 12 of a measuring apparatus. The other end of the optical fiber 11 was bonded to a sensing membrane 7. Further on the sensing membrane 7, an ion exchange membrane was placed as the chloride ion-concentrating means 8. The main body 12 of the measurement apparatus comprised therein a laser as an excitation light source, a detection system, and an electric circuit. The tip of the optical fiber 11 was dipped into the sample solution s in a container 13.

The optical sensor of this Example was prepared by dipping the tip of the optical fiber into the same aqueous polyacrylamide solution as in Example 8, irradiating the polyacrylamide through the optical fiber to cause polymerization, dipping the resulting polymerized membrane into the same aqueous solution of fluorescent dye as in Example 8 to immobilize the fluorescent dye thereon, and bonding an ion exchange membrane 8 to the polymerized membrane in the same manner as in Example 8.

The excitation light from the main body 12 of the measurement apparatus was introduced through the optical fiber 11 to the sensing membrane 7 at the tip of the optical fiber to excite the fluorescent dye immobilized onto the sensing membrane 7 to emit fluorescence. A portion of the fluorescence was transmitted through the optical fiber 11 to the measurement apparatus in the main body 12, and the intensity of the fluorescence was measured by the detection system.

The chloride ion concentration was measured by the degree of the fluorescence quenching in the same manner as in Example 8. Continuous measurement of chloride ion was also achieved by inserting the tip of the optical fiber into a flow of a sample solution s.

EXAMPLE 10

FIG. 9 illustrates a constitution of still another embodiment of the present invention. A planar substrate 14 was a plate of glass (BK 7) of 20 mm square and 5 mm thick, which formed an optical waveguide by vapor-depositing an aluminum thin film of 10 μm thick on the back face f1 thereof and covering the front face f2 of the glass plate with a sensing membrane 7 composed of polyacrylamide which has a fluorescent dye composed of 3,6-bis(dimethylamino) -10-alkylacridinium halide immobilized thereon. Further on the sensing membrane 7, an ion exchange membrane 8 was overlaid as a chloride ion concentrating means. A sample solution s was brought into contact with the ion exchange membrane 8. An argon-ion laser device 1 as the excitation light was placed at the lateral face side from the planar substrate 14 (in a thickness direction). A photodetector 4 was placed at the other lateral portion in counterposition to the argon-ion laser 1 via a band-pass filter 6 placed before the photodetector 4.

Excitation light of 488 nm from the argon-ion laser device 1 entered the planar substrate 14 from the lateral face (in a thickness side) and reached the other lateral face by repeating total reflection at both the surface f2 bonded to the sensitive membrane 7 and the surface f1 having a vapor-deposited thin film. On the face f2 bonded to the sensitive membrane 7, the fluorescent dye in the sensing membrane 7 was excited by the evanescent light generated by the excitation light to emit evanescent fluorescence. A portion of the emitted evanescent light, after repetitive total reflection at both the vapor-deposited face and the sensitive membrane-bonded face, was led out to the outside to reach the photodetector 4 through the band-pass filter 6, thereby the light intensity being measured.

The chloride ion concentration was measured in the same manner as in Example 8 by the degree of fluorescence quenching. When the sample solution s was flowing along the ion exchange membrane 8, the chloride ion concentration in the sample solution s could be measured continuously.

The fluorescent dye of the present invention is capable of detecting halogen ions with high sensitivity as conventional fluorescent dyes, and moreover, it enables selective detection of chloride ion in coexistence of halide ions.

The analytical method of the present invention employing the above fluorescent dye enables continuous measurement of chloride ion. It also enables precise measurement of chloride ion in coexistence of iodide ion, which has been impracticable by conventional techniques.

A chemical sensor of the present invention is capable of optical measuring of chloride ion with high precision and selectively without interference of other halogen ion. The sensor is widely useful for measurement of chloride ion in starting materials, intermediate products, and final products of chemicals, for analysis or monitoring of cooling water and waste water in industrial plants, and for sensing of chloride ion in environmental water such as underground water and river water, and in biological samples such as blood and intracellular fluid, and so forth.

What is claimed is:

1. A fluorometric analytical method for detecting a chloride ion concentration in a sample liquid comprising the steps of:
providing a fluorescent dye represented by the following formula (1) or (2) in an aqueous form

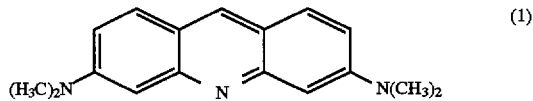

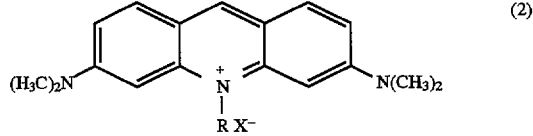

wherein R is alkyl having 1 to 30 carbon atoms, and $X^-$ is a halogen ion;
bringing said aqueous fluorescent dye into contact with chloride ions in a sample liquid; and
measuring the amount of fluorescence of said fluorescent dye that is quenched by the chloride ions wherein said method is substantially free from interference from other halide anions.

2. The fluorometric analytical method according to claim 1, wherein the fluorescent dye represented by Formula (2) is immobilized on a support, and the support is brought into contact with said sample liquid, whereby a chloride ion concentration is measured continuously without consuming the fluorescent dye.

3. The fluorometric analytical method according to claim 1, wherein the $X^-$ in Formula (2) is a bromide.

4. The fluorometric analytical method according to claim 1, wherein the step for providing the fluorescent dye in an aqueous form comprises dissolving the fluorescent dye in an aqueous liquid.

5. The fluorometric analytical method according to claim 4, wherein the aqueous liquid is the sample liquid.

6. The fluorometric analytical method according to claim 1, wherein the step for providing the fluorescent dye in an aqueous form comprises the steps of:
immobilizing said fluorescent dye on a surface of a polymer membrane; and
immersing said polymer membrane having the immobilized fluorescent dye thereon in an aqueous liquid.

7. The fluorometric analytical method according to claim 6, wherein the aqueous liquid is the sample liquid.

8. A chemical sensor for measuring a chloride ion concentration comprising a sensitive membrane in a transparent sample cell, wherein said sensitive membrane contains an immobilized fluorescent dye of the following formula (2) on a surface of the membrane,

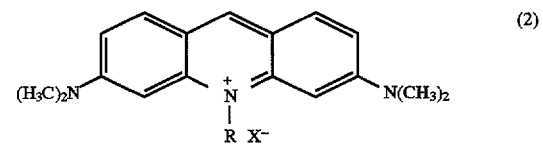

wherein R is alkyl having 1 to 30 carbon atoms, $X^-$ is a halogen ion and wherein fluorescence of the fluorescent dye is quenched by chloride ion without substantial interference from other halide anions.

9. The chemical sensor according to claim 8, wherein the sensitive membrane is a polymer membrane.

10. The chemical sensor according to claim 9, wherein the polymer membrane is composed of polyacrylamide.

11. The chemical sensor according to claim 8, comprising said sensitive membrane and an optical waveguide, wherein the sensitive membrane is set at the end or a lateral face of the optical waveguide.

12. The chemical sensor according to claim 11, wherein the sensitive membrane immobilizing the dye is placed at an end of the optical waveguide.

13. The chemical sensor according to claim 12, wherein the optical waveguide comprises an optical fiber.

14. The chemical sensor according to claim 12, wherein the optical waveguide is constituted of a planar substrate.

15. A chemical sensor for measuring a chloride ion concentration, comprising a support having a fluorescent dye immobilized on a surface of the support, and a chloride ion concentrating means bonded to the surface of the support, the fluorescent dye being represented by the formula (2)

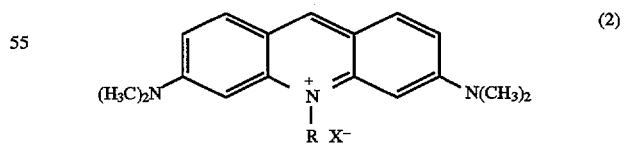

wherein R is alkyl having 1 to 30 carbon atoms, $X^-$ is a halogen ion and wherein fluorescence of the fluorescent dye is quenched by chloride ion without substantial interference from other halide anions.

16. The chemical sensor according to claim 15, comprising an optical waveguide bonded to the support.

17. The chemical sensor according to claim 16, wherein the optical waveguide comprises an optical fiber.

18. The chemical sensor according to claim 17, wherein the support is bonded to an end or a lateral face of the optical fiber.

19. The chemical sensor according to claim 16, wherein the optical waveguide is constituted of a planar substrate.

20. The chemical sensor according to claim 19, wherein the support is bonded to a surface of the planar substrate.

21. The chemical sensor according to claim 15, wherein the support is a polymer membrane.

22. The chemical sensor according to claim 21, wherein the polymer membrane is composed of polyacrylamide.

23. The chemical sensor according to claim 15, wherein the chloride ion concentrating means is an ion exchange membrane.

* * * * *

UNITED STATES PATENT AND TRADEMARK OFFICE
CERTIFICATE OF CORRECTION

PATENT NO. : 5,691,205

DATED : November 25, 1997

INVENTOR(S): YUJI KAWABATA ET AL.

It is certified that error appears in the above-identified patent and that said Letters Patent is hereby corrected as shown below:

ON THE TITLE PAGE AT [56]
  Other Publications, Under Urbano et al., "Detrmination" should read --Determination--.

ON THE TITLE PAGE AT [56]
  Attorney, Agent, or Firm, "Fitzpatrick Cella Harper & Scinto" should read --Fitzpatrick, Cella, Harper and Scinto".

COLUMN 1
  Line 42, "indespensable" should read --indispensable--.

COLUMN 8
  Line 59, "1.00." should read --1.00.
                    Table 1--.

UNITED STATES PATENT AND TRADEMARK OFFICE
CERTIFICATE OF CORRECTION

PATENT NO. : 5,691,205

DATED : November 25, 1997

INVENTOR(S) : YUJI KAWABATA ET AL.

It is certified that error appears in the above-identified patent and that said Letters Patent is hereby corrected as shown below:

COLUMN 12
    Line 8, "spreaded" should read --spread--.
    Line 54, "10-alkylacrtdinium" should read --10-alkylacridinium--.

Signed and Sealed this

Nineteenth Day of May, 1998

Attest:

BRUCE LEHMAN

Attesting Officer        Commissioner of Patents and Trademarks